United States Patent [19]

Clingman, Jr. et al.

[11] Patent Number: 5,115,687

[45] Date of Patent: May 26, 1992

[54] METHOD AND APPARATUS FOR TAKING A PROPORTIONAL SAMPLE OF FLOWING GAS IN A LINE

[75] Inventors: William H. Clingman, Jr., University Park; Lyn R. Kennedy, Ovilla, both of Tex.

[73] Assignee: Badger Meter, Inc., Milwaukee, Wis.

[21] Appl. No.: 665,354

[22] Filed: Mar. 5, 1991

Related U.S. Application Data

[60] Continuation-in-part of Ser. No. 395,135, Aug. 16, 1989, Pat. No. 5,016,482, which is a continuation-in-part of Ser. No. 143,126, Jan. 12, 1988, abandoned, which is a continuation-in-part of Ser. No. 33,919, Apr. 1, 1987, abandoned, which is a continuation of Ser. No. 688,910, Jan. 4, 1985, abandoned, which is a continuation-in-part of Ser. No. 518,963, Aug. 1, 1983, abandoned, which is a division of Ser. No. 272,204, Jun. 10, 1981, Pat. No. 4,396,299.

[51] Int. Cl.$^5$ .......................................... G01N 1/22
[52] U.S. Cl. ................................. 73/863.61; 73/863.03
[58] Field of Search ........... 73/863.01, 863.02, 863.03, 73/863.4; 137/100

[56] References Cited

U.S. PATENT DOCUMENTS

| | | | |
|---|---|---|---|
| 1,558,529 | 10/1925 | Wünsch | 137/100 |
| 3,377,867 | 4/1968 | Nitescu | 73/863.03 |
| 3,777,562 | 12/1973 | Clingman, Jr. | 374/37 |
| 3,930,414 | 1/1976 | Russell | 73/863.03 |
| 4,125,018 | 11/1978 | Clingman, Jr. | 374/37 |
| 4,125,123 | 11/1978 | Clingman, Jr. | 374/37 X |
| 4,285,245 | 8/1981 | Kennedy | 73/861 |
| 4,396,299 | 8/1983 | Clingman, Jr. et al. | 374/37 |
| 4,532,814 | 8/1985 | Lalin | 73/863.03 |
| 4,596,156 | 6/1986 | Shimizu et al. | 73/863.61 X |
| 4,681,530 | 7/1987 | Huber | 137/100 X |

FOREIGN PATENT DOCUMENTS

| | | | |
|---|---|---|---|
| 668227 | 8/1963 | Canada | 73/863.03 |
| 3316854 | 11/1984 | Fed. Rep. of Germany | 73/863.02 |

OTHER PUBLICATIONS

"A Proportionate Gas Sampler", *ISA Journal;* May 1963; pp. 73–76; D. L. Hammond.

"Orifice Metering of Natural Gas"; American Gas Association (AGA) Report No. 3 (ANSI/API 2530), Mar. 1978; pp. 1–88.

*Primary Examiner*—Tom Noland
*Attorney, Agent, or Firm*—Johnson & Gibbs

[57] ABSTRACT

Disclosed is a method and apparatus for taking a constantly proportional flowing sample of gas flowing through a main line having a first flow restriction therein. According to the teachings of the present of invention, such an apparatus includes a sample line connected to the main line so as to draw a flowing sample of gas from the main line at a point upstream from the first flow restriction; a second flow restriction in the sample line, the second flow restriction being very small relative to the main and sample lines and the first flow restriction; and structure that equalizes the pressure downstream of the first and second flow restrictions.

6 Claims, 3 Drawing Sheets

METHOD AND APPARATUS FOR TAKING A PROPORTIONAL SAMPLE OF FLOWING GAS IN A LINE

This is a continuation-in-part of application Ser. No. 07/395,135, filed Aug. 16, 1989, and now U.S. Pat. No. 5,016,482 which is a continuation-in-part of application Ser. No. 07/143,126, filed Jan. 12, 1988, now abandoned, which is a continuation-in-part of application Ser. No. 033,919, filed Apr. 1, 1987, now abandoned, which is a continuation of application Ser. No. 688,910, filed Jan. 4, 1985, now abandoned, which is a continuation-in-part of application Ser. No. 518,963, filed Aug. 1, 1983, now abandoned, which was a division of application Ser. No. 272,204, filed Jun. 10, 1981, now U.S. Pat. No. 4,396,299, issued Aug. 2, 1983.

BACKGROUND OF THE INVENTION

1. Field of the Invention

The present invention relates to measuring the total energy flow rate of combustible gas and, more particularly, to a method of taking a flowing sample which is proportioned to the total energy flow rate.

2. History of the Prior Art

The dollar value of BTUs contained in natural gas, and other combustible gases, has increased the need to measure accurately the total energy flow rate of gas moving through pipe line systems, both at points near the point of use of the gas, and at points which may be remote from the point of use. The conventional methods for determining total energy flow rate at a point in a gas pipeline generally involve the simultaneous (or at least contemporaneous) measurement of several gas parameters which are then employed as inputs into calculations ultimately producing a value for energy flow. For example, one approach is to measure the pressure drop across an orifice plate in the line to obtain a starting point for calculation of flow rate, and to simultaneously measure the temperature and pressure of the flowing gas and its composition at the time (the latter being measured by a gas chromatograph). The composition, pressure and temperature measurements provide the data necessary for calculation of the density of the gas at the orifice plate. The calculated density and the before mentioned pressure drop across the orifice plate provide the data necessary for calculation of the volumetric flow rate. The gas composition measurement, taken together with the known heat of combustion values for various compounds and elements, enables one to calculate the heat of combustion per unit volume. Finally, the calculated heat of combustion per unit volume can be multiplied by the calculated volumetric flow rate to give a value for energy flow rate.

It can be seen that this approach and other similar conventional approaches which involve the making of multiple measurements of gas properties or parameters suffer from the apparent disadvantage that each measurement or type of measurement involves measurement errors. The errors of the multiple measurements accumulate and contribute an error in the final calculated value, which error may be quite sizable. In addition, each measurement made on the gas involves a measuring entity comprising some quality of equipment which must be maintained, and further involves periodic calibrating of that equipment to the desired or best possible accuracy. Furthermore, such approaches, to the extent that they involve hand calculations, also present opportunities for calculation errors.

SUMMARY OF THE INVENTION

In accordance with the present invention, a method is provided for measuring total energy flow rate of combustible gas flowing in a line. The method involves making only a single measurement of a parameter which stands in constant proportion to the total energy flow rate of the moving gas. The invention involves two basic steps: The first step involves the taking of a continuous or flowing sample of the gas flowing in the pipeline, which sample is a constant fraction of the gas flowing through the line. The second step preferably involves burning of the sample with an amount of air which results in the combustion temperature being maximized. When the burning occurs under conditions which maximize the combustion temperature, then the air flow rate producing that condition is proportional to the energy flow in the gas flowing through the main pipeline. In a sense, the sample of combustible gas is "titrated" with air. The present invention, thus in part, makes use of techniques disclosed and claimed in Clingman, U.S. Pat. Nos. 3,777,562 issued Dec. 11, 1973; 4,062,236 issued Dec. 13, 1977; 4,125,018, issued Nov. 14, 1978; and 4,125,123 also issued Nov. 14, 1978. Furthermore, the present invention preferably makes use of a flow measurement system for determining air flow of the kind disclosed and claimed in Kennedy, U.S. Pat. No. 4,285,245, issued Aug. 27, 1981.

As is set forth hereinafter, the second step in the determination of the total energy flow rate of combustible gas flowing in a line may alternately comprise forming a stoichiometric mixture of air and the sample of combustible gas and burning it. The rate of air flow sufficient to produce the stoichiometric mixture is also directly proportional to the energy flow rate in the main pipeline. As a variant on this latter step, an excess of air on stoichiometric quantity of air may be flowed to the sample flame, and the residual oxygen flow in the exhaust gas measured. The level of residual oxygen flow is also a function of the energy flow rate in the main pipeline.

Since the present invention involves the making of only a single measurement, it represents a material advance in the accuracy of determination of total energy flow rate of gas moving through a line, because the stacking up or accumulation measurement errors inherent in methods involving the measurement of multiple parameters are eliminated.

The taking of the proportionally constant sample in accordance with the present invention may be performed in any satisfactory manner. In some situations, a simple branching of the main gas flow pipeline into a main line and a sample line using conventional hardware may be adequate to provide for the proportionally constant sampling. In most situations, however, such a simple arrangement of hardware will not suffice to provide the uniformity of the proportional sampling desired.

Accordingly, it is preferred that the equipment for the continual taking of a proportionate sample of the gas flowing through the line in accordance with the method of the invention includes an orifice plate flow meter in the main gas pipeline, a sample line tapped into the main pipeline upstream from the orifice plate, an orifice plate in the sample line, and equipment for adjusting the pressure downstream of both orifice plates to the same value. The downstream pressure equalizing equipment may take any one of several forms as will be made clear in the discussion of the detailed embodiments which follow.

With special respect to the subject matter of this case as distinguished from its parent, in embodiments of the invention the sample line orifice diameter is set much smaller than the main line, sample line, and main line orifice diameters. Such a setting of values causes the sample line diameter to become less and less critical as main line flow increases, renders the split (defined as main line flow divided by sample line flow) independent of the main line flow and gas composition, and generally provides an improved method and apparatus for taking proportional samples of flowing gas in main lines having Reynolds numbers that exceed 100,000.

As will be set forth hereinafter, a consideration of the orifice equations will reveal that when (a) the pressure drop across each orifice plate is adjusted and maintained at a uniform level; (b) the gas temperature and composition at each orifice plate are uniform; and (c) the upstream pressures are uniform (all of which conditions being met in accordance with the invention), the ratio of flow rates between the main gas flow pipeline and the sample line are in a fixed ratio, dependent primarily on relative orifice area.

While it is possible to measure the pressure drops across the main line and sample line orifice plates and to calculate from the pressure drop measurements the respective flow rates, this is not strictly necessary for the routine practice of the invention. What is of interest is not so much the value of the flow rates as the circumstance that the sample line gas flow rate is a constant proportion of the main line gas flow rate, assuming, of course, that the equipment has been properly calibrated.

As mentioned above, the sample flowing through the sample line is combusted or burned with air. In a preferred embodiment the flow rate of the air for combustion is measured. The air flow rate is varied or adjusted so that the combustion temperature is at a maximum. When this condition is met, the air flow rate is directly proportional to the flow rate of energy in the main pipeline. While the maximum temperature method is presently preferred, the alternate methods involving stoichiometric mixtures or deliberate excesses of combustion air may also be employed.

As a matter of equipment for carrying out the method of the invention, the several apparatuses shown in above mentioned U.S. Pat. Nos. 4,125,123; 4,125,018; 4,062,236 and 3,777,562 may be used in various embodiments, if suitably modified. In this connection, it should be noted that in said patents a number of the embodiments perform a flow rate measurement step on the gas stream rather than on the air stream, although in each case this procedure is a matter of choice. When such equipment is used in the practice of the present invention, the flow rate measurement of the air stream is the measurement which is of interest and which is, as a practical matter, the stream which must be measured. Thus, persons with ordinary skill in the art will understand how to modify or alter the equipment shown in the above listed patents to accommodate it to the practice of the present invention.

It should also be noted that the air flow rate which produces a maximum adiabatic flame temperature is also, within very close limits, equal to the air flow rate which produces a stoichiometric mixture with the particular gas composition flowing through the main pipeline.

This circumstance leads to the alternate methods of performing the second step of the invention. Thus, starting with an excess of air, the air flow rate of the air may be slowly lowered and monitored by an oxygen detector in the exhaust gas from the flame where the sample is burned. When the oxygen detector indicates a sharp decrease in oxygen in the exhaust gas, it is then known that the air flow rate is sufficient to produce a stoichiometric mixture. As another variant manner in performing the second step, an excess of air may be flowed to combust with the sample of combustible gas. The oxygen flow in the exhaust gas from the flame can be monitored, and the level of excess flow or remnant air in the exhaust gas stream is a linear function of the energy flow rate in the sample stream and in the gas stream in the main pipeline.

From the foregoing it can be seen that the primary object of the invention is a method and apparatus for accurately and conveniently measuring the total energy flow rate of a gaseous fuel moving through a line.

Another object of the invention is to provide a method and apparatus for taking a continual sample of gas from a gas flowing through a main line, which sample is a constant proportion of the gas flowing through the main line.

Still another object of the present invention is to provide a method and apparatus for dividing a flow gas stream into constantly proportionate streams.

Still another object of the present invention is to provide a method and apparatus whereby the energy flow rate in a gas flowing through a line may be readily determined without resorting to a multiplicity of measurements.

Still another object of the present invention is to provide a method and apparatus especially well suited to take samples from transmission pipelines.

The manner in which the foregoing and other objects are attained, together with other objects and purposes of the invention, may best be understood by considering the detailed description which follows, together with the accompanying drawings.

DESCRIPTION OF THE PREFERRED EMBODIMENT

Figure 1:
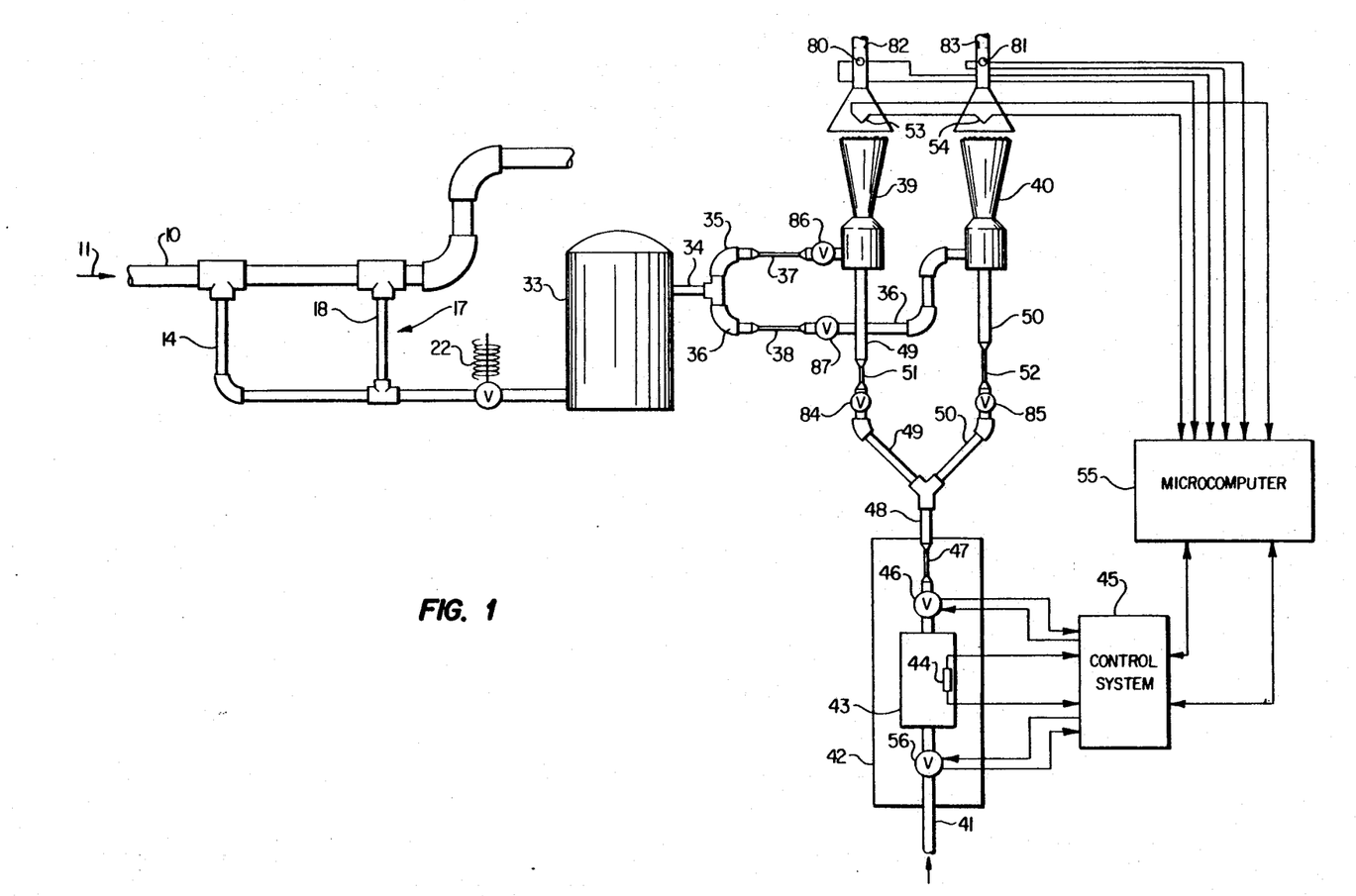
FIG. 1 is a diagrammatic elevational view of a system constructed in accordance with the invention and operating to practice the method aspects of the invention.
Figure 2:
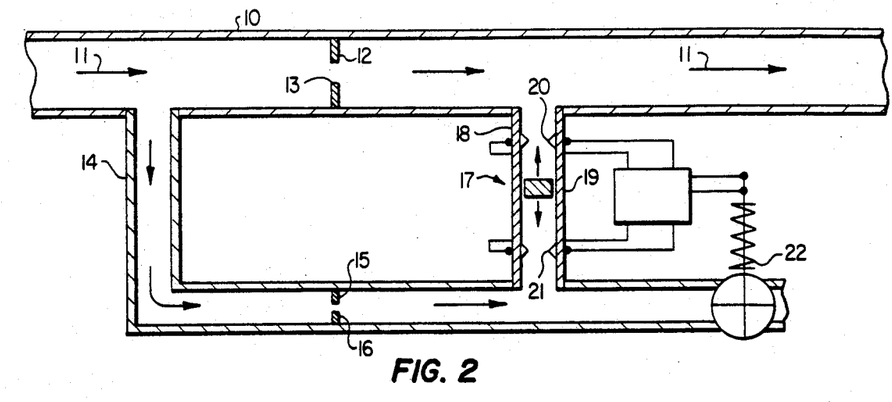
FIG. 2 is a diagrammatic elevational view of proportionate sample gathering equipment of the system of FIG. 1.

Attention is first directed to FIGS. 1 and 2 which illustrate a method and equipment of the invention in one preferred form. In these figures a main gas pipeline is designated 10 and the flow of gas through the pipeline 10 from left to right is indicated by arrow 11. In the pipeline 10 is mounted an orifice plate 12 having an orifice opening 13. Upstream of the orifice plate 12 a branch line 14 is tapped into main line 10. The branch line 14 also has an orifice plate 15 mounted therein, and the orifice plate 15 has an orifice opening 16. The equipment described to this point thus consists of the main pipeline 10 having the orifice plate 12 positioned therein, and the branch line 14 having orifice plate 15 positioned therein.

FIGS. 1 and 2 are diagrammatic and the combination of the branch line 14 and a branch line 18 (hereinafter described) is intended to represent both pipe taps and flange taps, it being understood that flange taps would be located in flanges which would support orifice plate 12 in a manner well known in the art. Pipe taps would be inserted into pipeline 10 essentially as illustrated in FIGS. 1 and 2.

For determining the rate of flow of a gas through the orifice 13 of the orifice plate 12, and the orifice 16 of the orifice plate 15, one employs the so-called "Hydraulic" equation, namely:

$$Q_s = KA\sqrt{2gh} \quad \text{(Equation No. 1)}$$

where
$Q_s$ = Quantity rate of flow at the average specific weight of measurement in cu ft per second
$K$ = Coefficient of discharge including velocity of approach factor corresponding to the condition of measurement
$A$ = Area of orifice in sq ft
$g$ = Acceleration due to gravity in ft per second per second
$h$ = Differential head in feet of the fluid flowing and at the average specific weight at the orifice

EQUATIONS FOR USE IN GAS MEASUREMENTS

In the measurement of most gases, the generally accepted practice is to express the flow in cubic feet per hour to a specific reference or base condition of pressure and temperature. The differential head is measured in inches of water, and the static pressure in lbs. per sq. in. The above-identified Hydraulic equation (Equation No. 1) can thus be arranged to give results directly in these units by substituting in the necessary values. It will then read $$Q_h = C'\sqrt{h_w p_f} \quad \text{(Equation No. 2)}$$

where
$Q_h$ = Quantity rate of flow at base conditions in cu ft/hr
$h_w$ = Differential pressure in inches of water
$p_f$ = Absolute static pressure, psia $C'$ = Orifice flow constant (this corresponds to what was formerly called the hourly coefficient) which is found by substituting the following values in Equation 1

$g = 32.17$ $$h = \frac{h_w \gamma_w}{12\gamma} \quad \text{(Equation No. 3)}$$

$\gamma_w = 62.37$ specific weight of water at 60° F. in lb/cu ft
$\gamma$ = Actual specific weight of gas at flowing conditions in lb cu/ft $$A = \frac{\pi d^2}{4 \times 144} \quad \text{(Equation No. 4)}$$

where
$d$ = Orifice diameter in inches, and
$Q_f = 3600 \, Q_s$ = Quantity rate of flow at flowing condition in cu ft/hr If one then takes the specific weight of dry air at 14.70 psia and 32° F. to be 0.08073 lb/cu ft then Boyle's and Charles' laws for gases will give $$\gamma = 0.08073 \frac{p_f}{14.7} \cdot \frac{492}{T_f} G \quad \text{(Equation No. 5)}$$

where
$T_f$ = Absolute flowing temperature in degrees Rankine, which is obtained by adding 460 to the flowing temperature in degrees Fahrenheit
$G$ = Specific gravity of the flowing gas, dry air = 1.000
NOTE—When determining the value of G the gas sample should not be dried, but reference air should be dried.

Making these substitutions in Equation No. 2 gives $$Q_f = 3600 \frac{\pi d^2}{4 \times 144} K \sqrt{2 \times 32.17 \cdot \frac{h_w}{12} \cdot \frac{62.37}{0.08073} \cdot \frac{14.7}{P_f} \cdot \frac{T_f}{492} \cdot \frac{1}{G}} \quad \text{(Equation No. 6)}$$

$$= 218.44 d^2 K \sqrt{\frac{h_w T_f}{p_f G}} \quad \text{(Equation No. 7)}$$

Again, using the combined laws of Boyle and Charles.

$$\frac{p_f Q_f}{T_f} = \frac{p_b Q_h}{T_b} \quad \text{(Equation No. 8)}$$

and $$Q_h = \frac{p_f Q_f T_b}{p_b T_f} \quad \text{(Equation No. 9)}$$

where
$p_b$ = Absolute pressure at reference or base condition,
$T_b$ = Absolute temperature at reference or base condition, °R Substituting the value of $Q_f$ from Equation No. 7 in Equation No. 9 gives $$Q_h = 218.44 d^2 K \frac{T_b}{p_b} \sqrt{\frac{h_w p_f}{T_f G}}$$ (Equation No. 10)

which also may be written $$Q_h = 218.44 d^2 K \frac{T_b}{p_b} \sqrt{\frac{1}{T_f G}} \sqrt{h_w p_f}$$ (Equation No. 11)

and, therefore, $$C = 218.44 d^2 K \frac{T_b}{p_b} \sqrt{\frac{1}{T_f G}}$$ (Equation No. 12)

NOTE—While the exactness of the physical factors used in obtaining Equation No. 12 from Equation No. 2 in no way warrants giving the constant 218.44 to five figures, it has been done here to assure greater consistency in the results calculated from this equation.

COEFFICIENTS OF DISCHARGE

In both the Equation Nos. 1 and 12, a discharge coefficient K appears. This has to be determined experimentally and is known in the art. The tests have shown that for any one type of pressure taps, K varies with D, the size of the pipe; d, the size of the orifice; $Q_s$, the rate of flow through the orifice; $\gamma$, specific weight; and $\mu$, the viscosity of the fluid flowing. If the fluid is a gas, this coefficient also varies with x, the ratio of differential to upstream pressure; and k, the ratio of specific heats of the gas.

In order to predict accurately what the coefficient of any orifice is going to be, all of the above-mentioned facts concerning the flowing fluid must be known. The relations between these functions can be somewhat simplified for application to commercial use and the coefficient shown to depend on the Reynolds number, acoustic ratio, pipe size, and orifice diameter ratio.

The Reynolds number is a dimensionless ratio and is expressed as $$R_d = \frac{V_f d}{12}$$ (Equation No. 13)

where $R_d$ = Reynolds number
$V_f$ = Velocity of the jet in the plane of the orifice in ft/sec
$\mu$ = Absolute viscosity in lb/ft sec
d = Actual diameter of the orifice, inches
$\gamma$ = Actual specific weight of gas in lb/cu ft The acoustic ratio is expressed as x/k where $$x = \frac{p_{f1} - p_{f2}}{p_{f1}},$$

the ratio of differential pressure to absolute inlet static pressure
where $p_{f1}$ = Absolute static pressure at upstream pressure tap, psi
$p_{f2}$ = Absolute static pressure at downstream pressure tap, psi and $$k = \frac{c_p}{c_v}.$$

the ratio of specific heat of the gas at constant pressure to specific heat of the gas at constant volume The orifice diameter ratio is expressed as $$\beta = d/D$$ (Equation No. 14)

where D = The actual internal pipe diameter in inches.

EMPIRICAL EQUATIONS FOR K

The values of K used in the flow equations can be calculated by empirical equations derived from tests.

These empirical equations may be written as follows

For FLANGE TAPS $$K_e = 0.5993 + \frac{0.007}{D} + \left[0.364 + \frac{0.076}{\sqrt{D}}\right]\beta^4 + 0.4\left[1.6 - \frac{1}{D}\right]^5$$

$$\left[(0.07 + \frac{0.5}{D} - \beta\right]^{5/2} -$$

$$\left[0.009 + \frac{0.034}{D}\right][0.5 - \beta]^{3/2} + \left[\frac{65}{D^2} + 3\right][\beta - 0.7]^{5/2}$$

(Equation No. 15)

For PIPE TAPS $$K_e = 0.5925 + \frac{0.0182}{D} + \left[0.440 - \frac{0.06}{D}\right]\beta^2 +$$

$$\left[0.935 + \frac{0.225}{D}\right]\beta^5 + 1.35\beta^{14} + \frac{1.43}{\sqrt{D}}(0.25 - \beta)^{5/2}$$

(Equation No. 16)

In the above equations $K_e$ = Coefficient of discharge when the Reynolds number is equal to 1,000,000d/15.

NOTE—In Equations 15 and 16 the signs of some of the terms with fractional exponents become negative for some values of $\beta$. In such cases these terms are to be neglected, or their value treated as zero, and where these terms are a factor to another term, the whole product is to be neglected.

For either pair of taps $$K_o = \frac{K_e}{1 + \frac{15E}{1,000,000d}}$$ (Equation No. 17)

where $K_o$ = The coefficient of discharge for infinite Reynolds number which will be the minimum value for any particular orifice and pipe size.

The value of E is given by the following equation $$E = d(830 - 5000\beta + 9000\beta^2 - 4200\beta^3 + B)$$ (Equation No. 18)

where $$B = \frac{530}{\sqrt{D}} \text{ for Flange Taps} \quad \text{(Equation No. 19)}$$

$$B = \frac{875}{D} + 75 \text{ for Pipe Taps} \quad \text{(Equation No. 20)}$$

Thus K for any value of $R_d$ can be calculated using the following equation $$K = K_o(1 + E/R_d) \quad \text{(Equation No. 21)}$$

The coefficients calculated from these equations apply to orifices, provided the pipe is not less than 1.6 inches inside diameter and the diameter ratio is between 0.10 and 0.75. Under these conditions coefficients calculated for Flange Taps by the above equations are subject to a tolerance of plus or minus 0.5% when the diameter ratio is between 15% and 70%. When the diameter ratio is less than 15% or greater than 70%, the tolerance is to be increased to plus or minus 1%. For Pipe Taps, the tolerance is plus or minus 1.5% for diameter ratios below 20% or above 67%.

ORIFICE FLOW CONSTANT, C'

To compute K and then C' for each meter by the direct use of these empirical equations would be too time-consuming for routine work; hence some simplification is necessary. A convenient way of making this computation is to write another equation for the orifice flow constant C', namely, $$C' = F_b F_\gamma Y \; F_{pb} F_{tb} F_{tf} F_g F_{pv} F_m F_a F_l \quad \text{(Equation No. 22)}$$

in which
- $F_b$ = Basic orifice factor
- $F_\gamma$ = Reynolds number factor
- $Y$ = Expansion factor
- $F_{pb}$ = Pressure base factor
- $F_{tb}$ = Temperature base factor
- $F_{tf}$ = Flowing temperature factor
- $F_g$ = Specific gravity factor
- $F_{pv}$ = Supercompressibility factor
- $F_m$ = Manometer factor
- $F_a$ = Orifice thermal expansion factor
- $F_l$ = Gage location factor

BASIC ORIFICE FLOW FACTOR, $F_b$

The basic orifice flow factor may be defined by the equation $$F_b = 218.44 d^2 K_o \frac{T_b}{P_b} \sqrt{\frac{1}{T_f G}} \quad \text{(Equation No. 23)}$$

This is not the same as Equation No. 12 because $K_o$ is the particular value of K when $R_d = \infty$. By using the values:

$T_b = T_f = 520° R$ $p_b = 14.73$ psia
and $G = 1.000$
Equation No. 23 reduces to $$F_b = 338.17 d^2 K_o \quad \text{(Equation No. 24)}$$

Now $K_o$ may be calculated from Equation Nos. 15, 17, 18, and 19 for Flange Taps, and from Equation Nos. 16, 17, 18 and 20, for Pipe Taps, and tables prepared for values of $F_b$ (Flange) and $F_b$ (pipe) (correct?) for various values of D and d. The steps in the values of D and d may be so spaced as to make possible linear interpolation of intermediate values.

REYNOLDS NUMBER FACTOR, $F_\gamma$

The Reynolds number factor F is introduced because in any actual case of metering the Reynolds number $R_d$ will have a finite value; hence the corresponding value of K will be somewhat greater than $K_o$. From Equation No. 21 one has as a definition.

$$F_\gamma = 1 + E/R_d \quad \text{(Equation No. 25)}$$

E can be calculated from Equation Nos. 18 and 19 for Flange Taps and Equation Nos. 18 and 20 for Pipe Taps. The value of the Reynolds number as given in Equation No. 13, is thus $$R_d = \frac{V_f d \gamma}{12\mu}.$$

$V_f$ can be calculated from an equation similar to Equation No. 7, since $$V_f = Q_f/3600 A = Q_s/A \quad \text{(Equation No. 26)}$$

then $$V_f = 11.125 K \sqrt{\frac{h_w T_f}{p_f G}} \quad \text{(Equation No. 27)}$$

However, before $V_f$ can be calculated, it is necessary that the value of K be known or assumed. A study of the variation in the value of K with changes in pipe sizes and Reynolds number over the range ordinarily encountered in the measurement of natural gas showed that for any selected values of $\beta$, this variation is within plus or minus 2%. If an average value of K were used for any diameter ratio this 2% variation in K would cause a maximum variation of only about 0.05% in the values of F $\gamma$. Tables are known giving these average values of K for Flange and Pipe Taps used for the calculation of $V_f$ in order to determine F $\gamma$. Linear interpolation should be used for determining intermediate values of K to be used in calculating $R_d$ by Equation No. 28.

A series of determinations of the viscosity of natural gas, made by the U.S. Bureau of Mines, and a survey of the composition of the gases measured with orifice meters in representative locations throughout the country, indicated that $\mu = 0.0000069$ lb/ft-sec is a fair average value. Using this value of $\mu$, and assuming $T_f = 520° R$, and $G = 0.65$, we have from Equation Nos. 13 and 27.

$$R_d = 12835 dK \sqrt{h_w p_f} \quad \text{(Equation No. 28)}$$

By combining Equation Nos. 25 and 28, $$F = 1 + \frac{E}{12835 dk \sqrt{h_w p_f}} \quad \text{(Equation No. 29)}$$

$$\text{If } b = \frac{E}{12835 dk} \quad \text{(Equation No. 30)}$$

then $$F = 1 = \frac{b}{\sqrt{h_w p_f}} \quad \text{(Equation No. 31)}$$

To compute the values of F, a series of values of b are computed for the several orifice diameters d with a given line size D. Values of K are available from known tables for these various ratios of d/D. Values of E are computed for the same values of d and D.

Equation No. 31 is suitable for use with natural gases having certain characteristics. When gases with other characteristics are to be measured Equation No. 31 should be adjusted as follows:

$$F\gamma = 1 + \frac{b}{\sqrt{h_w p_f}} (F_c) \quad \text{(Equation No. 32)}$$

where $F_c$, a multiplier, is determined as follows:

when viscosity is expressed as $$\mu \text{ in lb/ft-sec } F_c = 5124 \mu_x \sqrt{\frac{T_f}{G}} \quad \text{(Equation No. 32A)}$$

$$\mu_{cp} \text{ in centipoise } F_c = 3.443 \mu_{cp} \sqrt{\frac{T_f}{G}} \quad \text{(Equation No. 32B)}$$

$$\mu_e \text{ in lb}(F)\text{-sec/ft}^2 F_c = 164800 \mu_c \sqrt{\frac{T_f}{G}} \quad \text{(Equation No. 32C)}$$

EXPANSION FACTOR, Y

When a gas flows through an orifice, the change in velocity and pressure is accompanied by a change in specific weight and a factor must be applied to the coefficient to allow for this change. This factor is known as the "Expansion Factor Y" and can be calculated from the following equations:

$$Y_1 = 1 - (0.41 + 0.35\beta^4)\frac{x}{k} \text{ for Flange Taps} \quad \text{(Equation No. 33)}$$

$$Y_1 = 1 - [0.333 + 1.145(\beta^2 + 0.7\beta^5 + 12\beta^{13})]\frac{x}{k} \quad \text{(Equation No. 34)}$$

for Pipe Taps where
 k = Ratio of specific heats.
 x =

$$\frac{p_{f1} - p_{f2}}{p_{f1}} = \frac{h_w}{27.70 p_{f1}}$$

$Y_1$ = The expansion factor based on the upstream absolute pressure. The values of $Y_1$ computed by these equations are subject to a tolerance varying from 0 when x=0, to plus or minus 0.5% when x=0.20. For larger values of x, a somewhat larger tolerance may be expected. The equation for Flange Taps may be used for a range of diameter ratios from 10% to 80%, while that for Pipe Taps may be used over a range from 10% to 70%.

If the static pressure is taken at the downstream pressure tap then the value of the expansion factor $Y_2$ can be calculated using the equation
for FLANGE TAPS $$Y_2 = Y_1 \sqrt{\frac{1}{1-x}} = \sqrt{1+x_2} - (0.41 + 0.35\beta^4)\frac{x_2}{k\sqrt{1+x_2}} \quad \text{(Equation No. 35)}$$

For PIPE TAPS $$Y_2 = \sqrt{1 + x_2} - [0.333 + 1.145(\beta^2 + 0.7\beta^5 + 12\beta^{13}]\frac{x_2}{k\sqrt{1+x_2}} \quad \text{(Equation No. 36)}$$

where $$x_2 = \frac{p_{f1} - p_{f2}}{p_{f2}} = \frac{h_w}{27.70 p_{f2}}$$

In some cases the means static pressure between upstream and downstream pressures is more useful, and if this is used, the expansion factor $Y_m$ can be calculated by
For FLANGE TAPS $$Y_m = Y_1 \sqrt{\frac{2}{2-x}} = \sqrt{1 + \frac{x_m}{2}} - (0.41 + 0.35\beta^4)\frac{x_m}{k\sqrt{1+\frac{x_m}{2}}} \quad \text{(Equation No. 37)}$$

where $$x_m = \frac{p_{f1} - p_{f2}}{p_{fm}} = \frac{h_w}{27.70 p_{fm}}$$

Natural gases are generally assigned a specific heat ratio k of 1.3. When the gases being measured have significantly different k values the desirability of using adjusted Y values can be determined as follows:

$$\text{Adjusted value of } Y_1 = 1 - (1 - Y_1)\frac{1.3}{k}$$

where
 $Y_1$ = value read from know Tables, such as Tables 6 and 10 of "Orific Metering of Natural Gas", AGA Report No. 3, 1978, American Gas Association, Arlington, VA; and
 K = specific heat ratio for gas in equation.

$$\text{Adjusted value of } Y_2 = (1/2)\frac{\text{Adjusted } Y_1 \text{ value}}{Y_1}$$

Wherein $Y_1$ and $Y_2$ are obtained from Tables set forth in "Orifice Metering of Natural Gas" (Supra)

PRESSURE BASE FACTOR, $F_{bp}$

The pressure base factor $F_{bp}$ is applied to change the base pressure from 14.73 psia, and is calculated by dividing 14.73 by the required (contract) absolute base pressure. The use of this factor is equivalent to substituting the (contract) absolute base pressure in Equation No. 23 in place of 14.73.

$$F_{pb} = 14.73/Pb \qquad \text{(Equation No. 38)}$$

where Pb = The required contract base pressure, psia.

TEMPERATURE BASE FACTOR, $F_{tb}$

The temperature base Factor $F_{tb}$ is applied where the base temperature is other than 60° F. and is calculated by dividing the required (contract) base temperature in degrees Rankine by 520°. The use of this factor is equivalent to substituting the contract absolute temperature base instead of 520° R in Equation No. 23.

$$F_{tb} = T_b/520 \qquad \text{(Equation No. 39)}$$

where $T_b$ = The required (contract) base temperature in degrees Rankine.

FLOWING TEMPERATURE FACTOR, $F_{tf}$

The flowing temperature factor $F_{tf}$ is required to change from the assumed flowing temperature of 60° to the actual flowing temperature $T_f$ and is determined by dividing 520° by the flowing temperature in degrees Rankine and taking the square root of the results. The use of this factor is equivalent to substituting the actual absolute flowing temperature in place of the assumed temperature of 520° R in Equation No. 23.

$$F_{tf} = \sqrt{\frac{520}{T_f}} \qquad \text{(Equation No. 40)}$$

where $T_f$ = Actual flowing temperature of the gas in degrees Rankine.

SPECIFIC GRAVITY FACTOR, $F_g$

The specific gravity factor $F_g$ is to be applied to change from a specific gravity of 1.0 to the real specific gravity of the flowing gas, and is obtained by taking the square root of 1 divided by the real specific gravity. The use of this factor is equivalent to substituting the real gravity for the assumed value of 1 in Equation No. 23.

$$F_g = \sqrt{\frac{1}{G}} \qquad \text{(Equation No. 41)}$$

G = Specific gravity of the flowing gas, air = 1.000

Almost universally the specific gravities used by the industry have been determined by relative density measurement made with gravity balances. The procedures have only required that the observations be adjusted so both the air and gas measurements reflected the same pressure and temperature. The fact that the temperature and pressures were not tied down has resulted in small variances in specific gravity determinations. Another small source of variance has been that atmospheric air has been used and its composition (also molecular weight and density) varies from place to place and time to time at any given location.

Where recording gravitometers are used and calibration is performed with reference gases, either "ideal" or "real" specific gravity can be obtained as the recorded specific gravity simply by the proper certification of the reference gas.

The relationship of the defined IDEAL SPECIFIC GRAVITY AND REAL SPECIFIC GRAVITY is established as follows:

$$PV = MRTZ \text{ or} \qquad (A)$$

$$PV = W \frac{g_s}{g_1} RTZ$$

where $M = \dfrac{g_s}{g_1}$ $$P = \frac{1}{v} W \frac{g_s}{g_1} RTZ \text{ or} \qquad (B)$$

$$P = \gamma \frac{g_s}{g_1} RTZ$$

where $\gamma = \dfrac{W}{V}$ since $\gamma = P \dfrac{g_1}{g_s}$ then equation (B) can be written $$P = p \frac{g_1}{g_s} \cdot \frac{g_s}{g_1} RTZ = pRTZ \text{ or restated} \qquad (C)$$

$$p = \frac{P}{RTZ} \qquad (D)$$

then $G = \dfrac{pg}{p_a}$ can be written $$G = \frac{\dfrac{P_g}{R_g T_g Z_g}}{\dfrac{P_a}{R_a T_a Z_a}} \text{ or}$$

$$G = \frac{P_g R_a T_a Z_a}{P_a R_g T_g Z_g} \qquad (E)$$

since $R = 1545.32$ then Equation (E) can be written $$G = \frac{P_g \quad \dfrac{1545.32}{\text{Mol Wt of Air}} \quad T_a Z_a}{P_a \quad \dfrac{1545.32}{\text{Mol Wt of Gas}} \quad T_g Z_g} = \frac{T_a Z_a}{T_g Z_g} \times \frac{\text{Mol Wt of Gas}}{\text{Mol Wt of Air}} = \frac{P_g T_a Z_a}{P_a T_g Z_g} \times \frac{\text{Mol Wt of Gas}}{\text{Mol Wt of Air}} \qquad (F)$$

since $G_i = \dfrac{\text{Mol Wt of Gas}}{\text{Mol Wt of Air}}$ $$G = \frac{P_g T_a Z_a}{P_a T_g Z_g} G_i \qquad (G)$$

where
P = Pressure in psia
V = Volume in cu ft
M = Mass
R = Universal gas constant = 1545.32 Mol Wt
T = Temperature in degrees Rankine
Z = Factor of Boyle's Law Deviation
w = Weight
$g_s$ = Gravitational Constant -continued
G1 = Actual value for local gravity
γ = Specific Weight
p = Density
G = Specific Gravity (real)
Gi = Specific Gravity (ideal)

SUPERCOMPRESSIBILITY FACTOR, $F_{pv}$

Boyle's law for gases states that the specific weight of a gas is directly proportional to the absolute pressure, the temperature remaining constant. All gases deviate from this law by varying amounts, and with the range of conditions ordinarily encountered in the natural gas industry the actual specific weight under the higher pressures is usually greater than the theoretical. When this deviation is represented by Factor Z, as above, and is applied to the development of the orifice meter flow formula an expression including the factor $\sqrt{1/Z}$ results. For convenience, this factor is termed the Supercompressibility Factor and designated as Fpv.

The method of supercompressibility factor evaluation bases the direct factor determination on the relating of the compressibility variation of various natural gases to that of a 0.600 specific gravity hydrocarbon gas.

Normal mixtures are defined as mixtures of essentially methane and ethane plus heavier hydrocarbon components, but not containing appreciable concentration of the much heavier natural gas hydrocarbons. The diluent content of any gas mixture to which the method is to be applied should be limited to 15 mol per cent carbon dioxide and 15 mol per cent nitrogen and actual tests are recommended for diluent content exceeding these quantities.

The specific gravity, carbon dioxide and nitrogen contents, in conjunction with the flowing pressure and temperature is used to determine the adjusted pressure and temperature necessary for relating any gas to the supercompressibility data of the 0.600 specific gravity, hydrocarbon gas.

Specific Gravity Method of Supercompressibility Factor Determination (A. G. A. Standard Method):

The adjusted pressure is obtained by multiplying the gage (?) pressure of the flowing gas by the pressure adjusting factor $F_p$ and the adjusted temperature is obtained by multiplying the absolute temperature of the flowing gas by the temperature adjusting factor $F_T$ and substracting 460 from this product. Adjusting factors $F_p$ and $F_T$ are calculated as follows:

$$F_p = \frac{156.47}{160.8 - 7.22G + K_p} \quad \text{(Equation No. 42)}$$

where $$K_p = M_c - 0.392M_n \quad \text{(Equation No. 43)}$$

and $$F_T = \frac{226.29}{99.15 + 211.9G - K_T} \quad \text{(Equation No. 44)}$$

where $$K_T = M_c + 1.681M_n \text{(Equation No. 45)}$$

and
G = Specific gravity of flowing gas
$M_c$ = Mol per cent carbon dioxide
$M_n$ = Mol per cent nitrogen $$\text{Adjusted Pressure} = P_f F_p = \text{psig} \quad \text{(Equation No. 46)}$$

$$\text{Adjusted Temperature} = T_f F_T - 460° \text{ F.} \quad \text{(Equation No. 47)}$$

After the adjusted pressure and the adjusted temperature are determined the supercompressibility factor $F_{pv}$ can be determined from available data, such as Table 16 in "Orific Metering of Natural Gas" (supra).

MANOMETER FACTOR, $F_m$, and LOCATION FACTOR, $F^1$

The manometer and location of factors are introduced to correct for the error in differential pressure indication in mercury manometer type gages caused by: (1) the weight of the gas column above the mercury; (2) the change in the specific weight of the mercury at temperatures other than the base temperature of 60° F.; and (3) the change in the specific weight of the mercury when subjected to gravitational forces departing from the international standard given for sea-level elevation at exactly 45° geographic latitude, i.e. 980.665 cm/sec/-sec.

The basic equations for the combined manometer and factors location are:

$$\text{Gas column weight correction} = [(\gamma m - \gamma g)/\gamma m]^{0.5}$$

$$\text{Mercury column temperature correction} = (\gamma m/\gamma m 60)^{0.5}$$

$$\text{Mercury column gravitation correction} = (g^1/g^s)_{0.5}$$

Combined Correction, $F_m F_1 =$ (Equation No. 48)

$$\left[\left(\frac{\gamma m - \gamma g}{\gamma m}\right)\left(\frac{\gamma m}{\gamma m 60}\right)\left(\frac{g_1}{g_s}\right)\right]^{0.5} =$$

$$\left[\frac{(\gamma m - \gamma g) \times g_1}{\gamma m 60 \times g_s}\right]^{0.5} =$$

where
g = Specific weight of gas displacing mercury, determined for the molecular weight of the gas at ambient temperature and static pressure psia at the gage.
m = Specific weight of the mercury at ambient temperature and standard gravity.
m60 = Specific weight of mercury at base temperature of 60° F. and standard gravity (0.489771 lb/in.³).
$g_1$ = Local gravity, cm/sec²
$g_s$ = Standard gravity at sea level, 45° latitude (980.665)

It will be noted g1 values are constants for any given measuring location, whereas other parameters to manometer factor selection are variables. Thus, in practice, the equation is best rewritten to isolate variables from constants.

$$F_m F_1 = \left(\frac{\gamma m - \gamma g}{\gamma m 60}\right)^{0.5} \left(\frac{g_1}{g_s}\right)^{0.5} \quad \text{(Equation No. 49)}$$

where

-continued $$F_m = \left(\frac{\gamma_m - \gamma_g}{\gamma_{m60}}\right)^{0.5} \quad \text{Manometer Factor,} \quad \text{(Equation No. 49a)}$$

and $$F_l = \left(\frac{g_l}{g_s}\right)^{0.5} \quad \text{Location Factor,} \quad \text{(Equation No. 49b)}$$

By substituting the density of mercury per cubic foot ($0.489771$ lb/in.$^3 \times 1728 = 846.324$) at base temperature of 60° F. and standard gravity of 980.665 cm/sec$^2$, the manometer factor equation resolves to:

$$F_m = \left(\frac{\gamma_m - \gamma_g}{846.324}\right)^{0.5} \quad \text{(Equation No. 50)}$$

where $$\gamma_g = \frac{2.699053 G_{pf}}{T_a Z}$$

$$\gamma_m = 846.324 \times [1 - 0.000101(T_a - 520)]$$

By substituting the standard gravity at sea level, 45° latitude (980.665 cm/sec$^2$) in equation No. 49b.

$$F_l = \frac{g_l}{980.665}\, 0.5 \quad \text{(Equation No. 51)}$$

The ambient value of gravity at any location is most accurately obtained from U.S. Coast and Geodetic Survey data, reference to aeronautical data or from Smithsonian Meteorological Tables. In the absence of better data, practical values of $g_l$ may be obtained by equation over the mid-latitudes, between 30° and 60°.

$$g_l = 980.665 + [0.087(°L - 45)] - 0.000094H$$

A curve fit equation covering latitudes from 0° to 90° may also be used:

$$g_l = 978.01855 - 0.0028247L + 0.0020299L^2 - 0.000015085L^3 - 0.000094H$$

where
°L = Degrees latitude
H = elevation in lineal feet above sea level
Other equations relating local gravity to latitude may be obtained from such sources as N. B. S. Nomograph 8.

NOTE—By substituting $\gamma_{wa}$ the specific weight of water at ambient temperature, for $\gamma_m$ and $\gamma_{w60}$ for $\gamma_{m60}$ the manometer factor may readably be determined when a water manometer is used.

ORIFICE THERMAL EXPANSION FACTOR, $F_a$

The Orifice Thermal Expansion Factor is introduced to correct for the error resulting from expansion or contraction of the orifice operating at temperatures appreciably different from the temperature at which the orifice was bored. The factor may be calculated from the following equation:
304 and 316 stainless steel $$F_a = 1 + [0.0000185(°F - 68)] \quad \text{(Equation No. 52)}$$

Monel $$F_a = 1 + [0.0000159(°F - 68)]\,°F. = \text{gas flowing temperature at orifice} \quad \text{(Equation No. 53)}$$

These formulas assume the orifice bore diameter, d, has been measured at a temperature of 68° F.

MEASUREMENT WHEN SPECIFIC WEIGHT IS KNOWN

In Equation No. 11, $T_f$ and $p_f$ have been introduced in an attempt to calculate $\gamma$, the specific weight of the gas at flowing conditions. The inaccuracy of Boyle's and Charles' laws, when applied to natural gas at high pressure, makes necessary the additional factor, $F_{pv}$.

Equation No. 5 may be reduced to the form $$\frac{p_f}{T_f} = \frac{14.7\gamma}{0.08073 \times 492 G} \quad \text{(Equation No. 5a)}$$

Substituting for $P_f/T_f$ in Equation No. 10

$$Q_h = 218.44 d^2 K \frac{T_b}{P_b} \sqrt{\frac{h_w}{G}} \sqrt{\frac{14.7\gamma}{0.08073 \times 492 G}} = 132.89 d^2 K \frac{T_b}{P_b G} \sqrt{h_w \gamma} \quad \text{(Equation 10a)}$$

where:
$K = K_o F \sqrt{\phantom{x}}$
$d^2 K_o = F_b/338.17$
$T_b = 520 F_{tb}$
$p_b = 14.73/F_{pb}$ Substituting the equivalent values in Equation No. 10a and inserting the expansion factor Y to make the equation complete for compressible fluids, $$Q_h = 132.89 \left(\frac{F_b}{338.17}\right) F_\gamma Y 520 F_{tb} \left(\frac{F_{pb}}{14.73 G}\right) \sqrt{h_w \gamma} = \frac{13.873}{G} F_b F_\gamma Y F_{tb} F_{pb} \sqrt{h_w \gamma}$$

If one lets $$C' = \frac{13.873}{G} F_b F_\gamma Y F_{tb} F_{pb}$$

then $$Q_h = C' \sqrt{h_w \gamma} \quad \text{(Equation No. 2a)}$$

MEASUREMENT IN WEIGHT UNITS

In certain industrial gas measurements, it may be desirable to measure gas in pounds. In that case, if the specific weight of the gas at flowing conditions is known, the formula for measurement becomes quite simple, since the rate of flow in pounds per hour equals the rate of flow in cubic feet at flowing conditions times the specific weight at flowing conditions in pounds per cubic foot, i.e., $W_h = Q_f$. Substituting the value of $Q_f$ from Equation No. 7, $$W_h = 218.44\gamma d^2 K \sqrt{\frac{h_w T_f}{p_f G}}$$ (Equation No. 7b)

From Equation No. 5, $$\frac{T_f}{p_f G} = \frac{0.08073 \times 492}{14.7\gamma}$$

Substituting in Equation No. 7b, $$W_h = 218.44\gamma d^2 K \sqrt{\frac{h_w \times 0.080723 \times 492}{14.7\gamma}} = 359.06 d^2 K \sqrt{h_w \gamma}$$ (Equation No. 10b)

Since, from previous equations $$d^2 K = \frac{F_b F_r}{338.17}$$

Substituting the equivalent values in Equation No. 10b and inserting the expansion factor Y to make the equation complete for compressible fluids, $$W_h = \frac{359.06}{338.17} F_b F_r Y \sqrt{h_w \gamma} = 1.0618 F_b F_r Y \sqrt{h_w \gamma}$$

If we let $C''' = 1.0618 F_b F_r Y$ $$W_h = C''' \sqrt{h_w \gamma}$$

Factors such as $F_{m'}$, $F_1$ and $F_a$ should be applied in weight flow measurements where applicable.

Thus, using the foregoing equations one can determine the gas flow through the orifice opening 13 of the orifice plate 12 and the orifice opening 16 of the orifice plate 15. Further, the subscripts set forth in the formulas, namely, 12 and 15, represent the orifice opening 13 and 16 of the orifice plates 12 and 15, respectively.

The equations for gas flow through orifices 13 and 16 of the orifice plates 12 and 15, respectively, are as follows:

$$Q_{12} = K_{12} A_{12} (2gh_{12})^{\frac{1}{2}}$$ (1)

$$Q_{15} = K_{15} A_{15} (2gh_{15})^{\frac{1}{2}}$$ (2)

Q = Rate of flow in cubic feet per second.
K = coefficient of discharge
A = orifice area
g = acceleration due to gravity
h = differential head across orifice As previously stated, the subscripts 12 and 15 associates with the parameters defined immediately preceding in the above equations and the equations hereinafter set forth refer to the orifice opening 13 and 16 and the orifice plates 12 and 15, respectively, and thus define the respective equations for each orifice plate. Further, the following equations are derived in the same manner as the before-described equations and explanations thereof as set forth in "Orific Metering of Natural Gas", AGA Report No. 3, 1978, American Gas Association, Arlington, Va.

Because of the metal structure the temperature at both of the orifice plates 12 and 15 will be the same. The gas composition is the same in both cases. The pressures on both sides of orifice 13 are also the same as the corresponding pressures across orifice 16. Thus, the gas properties on both sides of the orifice plates 12 and 15 are identical in the two cases. The ratio of the two flows is then given by $Q_{15}/Q_{12}$. Further, since the acceleration due to gravity (i.e., g is the same for both the orifice plates 12 and 15,) and the differential head across the orifices 13 and 16 are equal, $Q_{15}/Q_{12}$ is represented by the following equation:

$$Q_{15}/Q_{12} = (A_{15}/A_{12})(K_{15}/K_{12})$$

The general equation for the discharge coefficient is $$K_i = \frac{K_i'}{1 + \frac{15E}{1,000,000d}}$$

where $K_i$ the coefficient of discharge for infinite Reynolds number which will be the minimum value for any particular orifice and pipe size j and $K_j$ = Coefficient of discharge when the Reynolds number is equal to 1,000,000d/15. Solving the above equations one determines that:

$$K_i = K_i'(1 + E_i/R_{di})$$

i = orifice reference number
$K_i' = 1,000,000d/15$
$R_{di}$ = Reynolds number = $V_i d_i \rho / \mu$
$d_i$ = orifice diameter
$V_i$ = jet velocity in the plane of the orifice
$\rho$ = gas density
$\mu$ = viscosity
$E_i$ is known to be defined as hereinbelow set forth.

Applying this equation to orifices 13 and 16 of orifice plates 12, 15, respectively, gives:

$$K_{12} = K_{12}'(1 + E_{12}/R_{d12})$$

and $$K_{15} = K_{15}'(1 + E_{15}/R_{d12})$$

$E_i$ in the equation for discharge coefficient is defined as follows:

$$E_i = d_i(830 - 5000 b_i + 9000 b_i^2 - 4200 b_i^3 + B_i)$$ (4)

$D_i$ = pipe diameter
$b_i = d_i/D_i$
where $B_i = 530/D_i^{\frac{1}{2}}$ for flange taps and
$B_i = (875/D_i) + 75$ for pipe taps The effective area of the jet in the plane of the orifice is $A_i K_i$.
Thus, $$V_i = Q_i / A_i K_i$$

It thus follows that $V_{12} = V_{15}$ and $R_{d12}/^d 12 = R_{d15}/^d 15$.

Now define the function F(b) as follows:

$$F(b_i) = (E_i/d_i) - B_i$$

Using the above equations the data tabulated below was calculated.

| b | F(b) |
|---|---|
| .7 | 299 |
| .6 | 163 |
| .5 | 55 |
| .4 | 1 |
| .3 | 27 |
| .2 | 156 |
| .1 | 416 |

The design equations for orifice 16 are now as follows:

FLANGE TAPS:
$F(b_{15}) + 530/(D_{15})^{\frac{1}{2}} = F(b_{12}) + 530/(D_{12})^{\frac{1}{2}}$ PIPE TAPS: $F(b_{15}) + 875/D_{15} = F(b_{12}) + 875/D_{12}$ $b_{15}$ and $D_{15}$ are chosen so as to minimize the flow through line 14 and to satisfy these equations.

Downstream from the orifice plates 12 and 15, respectively, main line 10 and branch line 14 are connected by pressure equalizing means designated generally as 17. In the embodiment of FIGS. 1 and 2 this means includes a line 18 interconnected between the main pipe line 10 and branch line or sample line 14. A piston 19 is positioned to move within the line 18. Microswitch points 20 and 21 are positioned in line 18 to be connected by piston 19 when it is in the line 18 in the immediate vicinity of the microswitch points 20 and 21. Downstream in line 14 from the point of interception of line 18 with line 14 there is mounted motorized valve 22.

The operation of the equipment described to this point is as follows:

Assuming that motorized valve 22 is closed, the situation will be that the upstream pressure on orifice plates 12 and 15 will be equal, but the downstream pressure will be unequal. It will be lower in the main line 10 than in branch line 14. In branch line 14 the pressure on the downstream side of orifice plate 15 will be substantially equal to the upstream pressure by reason of the closed condition of valve 22. Under these circumstances piston 19 will move towards microswitch point 20 and will make the circuit through microswitch point 20. This event actuates motorized valve 22 to open and it will eventually open sufficiently so that the pressure on the downstream side of the orifice plate 15 will be lower than that on the downstream side of the orifice plate 12 in main line 10. These conditions will cause piston 19 to move towards microswitch points 21, and upon closing the circuits through the microswitch points 21, will actuate motorized valve 22 to close. Upon closure of the valve 22 the first described set of conditions in the operations will exist once again. The piston 19 thus migrates back and forth between microswitch points 20 and 21 for alternately opening and closing the motorized valve 22. Thus, on the average, the pressure downstream of orifice plate 12 and orifice plate 15 is equal, even though at any particular moment the downstream pressures may in fact be unequal.

Figure 3:
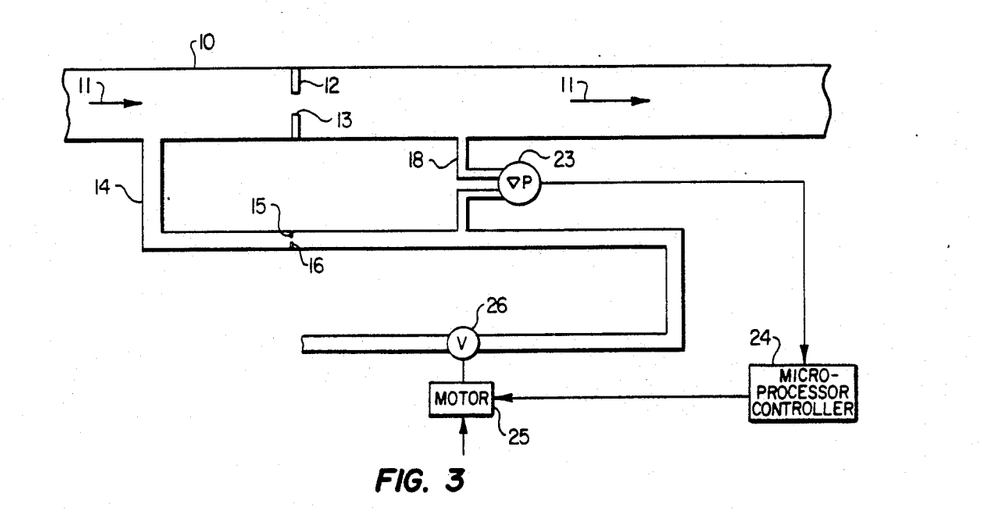
FIG. 3 is a diagrammatic elevational view of an alternate type of equipment for gathering proportionate samples in accordance with the invention.

Attention is now directed to FIG. 3 which shows another set of equipment for accomplishing a division of the gas stream into that flowing in the main pipe line and the proportionate fraction flowing in the branch line 14. In FIG. 3 the same reference characters are used for substantially identical parts.

The embodiment of FIG. 3 a differential pressure gauge or meter 23 is interposed in line 18 to compare the downstream pressure in main pipe line 10 and branch line 14. A comparison signal is sent to a microprocessor controller 24 where it is conventionally processed to send a signal to motor 25 of motor driven valve 26 to open or close the valve 26 in a manner to bring the two downstream pressures to equality.

Figure 4:
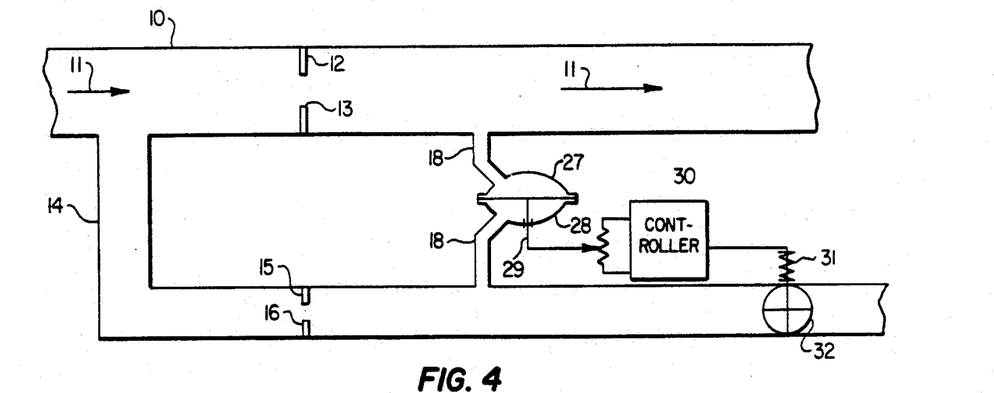
FIG. 4 is a diagrammatic elevational view of another alternate type of equipment for gathering proportionate samples in accordance with the invention.

In FIG. 4 there is illustrated still another set of equipment for performing the proportionate sample taking function. In the embodiment of FIG. 4 there is interposed in line 18 a housing 27 having a diaphragm 28 connected across the interior thereof. A follower 29 is connected to the diaphragm 28 and passes through an opening in the wall of housing 27. The follower 29 carries a wiper working on the slide wire of a potentiometer associated with a control box 30 which generates a signal which is addressed to a motor 31 of a motor controlled valve 32. When there is an imbalance in downstream pressures in lines 10 and 14 the diaphragm 28 will be moved upwardly or downwardly and its follower 29 will move to a different point on the slide wire of controller 30.

Figure 5:
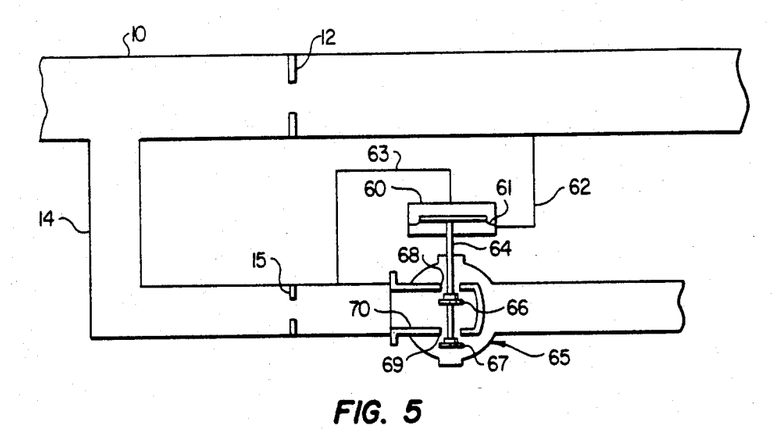
FIG. 5 is a diagrammatic elevational view of yet another alternate type of equipment for gathering proportionate samples in accordance with the invention.

Attention is now directed to FIG. 5 which illustrates still another means for establishing the pressure downstream of orifices 13 and 16 at the same level. A diaphragm housing 60 is provided surrounding a flexible diaphragm 61. The lower side of the housing 60 is connected by a line 62 to the main pipeline 10 at a point downstream from the orifice 13. The upper side of the housing 60 is connected by a line 63 to line 14 at a point downstream of the orifice 16. Thus, the diaphragm 61 is in pressure communication with the two pressures of interest, those just downstream of the orifice plates 12 and 15. The position of the diaphragm 61 with the housing 60 is thus a function of the two downstream pressures.

A control rod 64 is connected to the diaphragm 61 and passes through an opening in the housing 60 and into a valve 65 provided in line 14. The control rod 64 carries valve plates 66, 67, which are seatable in valve openings 68, 69, respectively, in a valve body 70.

In operation, if the downstream pressure in main line 10 is greater than that in line 14, the diaphragm 61 tends to close the valve 65 and increase the pressure in the line 14. If the downstream pressure in the line 14 is greater, the diaphragm 61 tends to open the valve 65 to reduce that pressure. Thus the two pressures of interest tend to be equalized.

Returning now to FIG. 1 it can be seen that downstream of the motorized valve 22 in line 14 there is provided a ballast or surge tank 33. The purpose of the ballast tank 33 is to smooth irregularities in flow resulting from excursions of the piston 19 in the line 18. The size of the ballast tank 33 need only be relatively large compared to the volume of the line 18 lying between the microswitch points 20 and 21. If equipment such as that shown in FIGS. 3 and 4 is employed in the sample taking and establishing equipment, the surges in flow are likely to be smaller than that involved in the equipment of FIG. 1, and it may thus be possible to dispense with the ballast tank 33 or to use a smaller tank.

The flowing gas sample is led from the ballast tank 33 through a line 34 to branch lines 35 and 36 where it is divided into two streams for delivery to two burners 39 and 40. A capillary 37 is in line 35 and a similar capillary 38 is in line.

Air is also delivered to the burners 39 and 40 through a specially designed flow-control system of the kind disclosed in above-mentioned U.S. Pat. No. 4,285,245. Air enters the system through a line 41 and passes through a flow control and measurement system 42. A major component of the system 42 is a motorized valve 56. The air then passes into a chamber 43 where its pressure is sensed by a transducer 44. Flowing air leaving the chamber 43 passes through a pressure regulator 46 and a capillary 47 into line 48. Line 48 is divided into lines 49 and 50 which lead to the burners 39 and 40, respectively. A capillary 51 is provided in the line 49 and a capillary 52 is provided in the line 50. Between line 48 and capillary 51 is a valve 84. Between line 50 and capillary 52 is a valve 85.

The rate of flow of energy into the flames of the burners 39 and 40, when their average temperature is at a maximum, is in direct proportion to the rate of air flow to the burners 39 and 40. This is an alternate way of stating the principal underlying the equipment just described and the equipment for determining the calorific value of a fuel gas described and shown in the above-listed patents. In effect, in the equipment shown in FIG. 1, the fuel flow to the burners 39 and 40 is "titrated" with air, using the maximum flame temperature as detected by thermocouples 53 and 54 to determine the end point. The measured rate of air flow is then in proportion to the rate of energy flow of the gas flowing in the conduit 14, and because of the proportionality of that gas flow rate to the gas flow rate in the main pipeline 10, the air flow rate as measured is also in constant proportion to the energy flow rate in main pipeline 10.

The detected thermocouple signals from thermocouples 53 and 54 are delivered to microcomputer 55 which processes the thermocouple signals and sends appropriate derivative signals to control system 45 of the flowmeter. In response to the signals it receives, the control system varies the setting of the pressure regulator 46 to increase or decrease the air flow to traverse it across the range of flow which produces a detectable maximum average temperature at the thermocouples 53 and 54. The motorized valve 56 is closed periodically by the control system and the pressure fall in the chamber 43 is detected by the pressure transducer 44 to provide a reading of the air flow rate, since the slope of the time decay of pressure in the capillary 47 is proportional to flow rate, as is explained in greater detail in U.S. Pat. No. 4,285,245.

In accordance with the invention other forms of flow measuring equipment may be employed for measuring the air flow rate. These alternate forms of air flow measurement include hot wire flowmeters, orifice plate flowmeters, rotometers, displacement meters of various sorts, and the like.

Instead of monitoring the flame temperature to establish a flow rate producing a maximum flame temperature, the oxygen flow, or lack thereof, in the exhaust immediately downstream from a burner may be monitored. Zirconium dioxide oxygen detectors are suitable for this purpose. When oxygen content in the exhaust gas is the detected parameter, only a single burner is employed, and the gas and air flow to the other burner in a unit may be terminated by suitable valves. In one embodiment employing exhaust gas oxygen monitoring, the desired end point is a sharp decrease in oxygen content in the exhaust gas, which means the air flow rate is producing a stoichiometric mixture. In another form of the invention in which oxygen flow in the exhaust gas is measured, the air flow rate is established at a rate in excess of the stoichiometric amount, and the residual, remnant or excess oxygen flow in the exhaust gas is monitored to yield a parameter which is a known or calculable function of the total energy flow rate in the main pipeline.

Returning now to FIG. 1, the equipment thereof for practicing the invention in accordance with the two alternate modes just discussed may be pointed out. In the exhaust gas lines above the burners 39 and 40 are mounted zirconium dioxide oxygen detectors 80 and 81, which are devices whose electrical output essentially switches from "on" to "off" when the stoichiometric point of oxygen content is crosses from rich to lean, thus providing a clear signal for that point. Also mounted in the exhaust lines are flowmeters 82 and 83, indicated diagrammatically as orifice plates in FIG. 1, although various sorts of flowmeters may be used. The flowmeters, in conjunction with the oxygen detectors, provide the data necessary for determining oxygen flow in the excess oxygen mode of operation.

Figure 6:
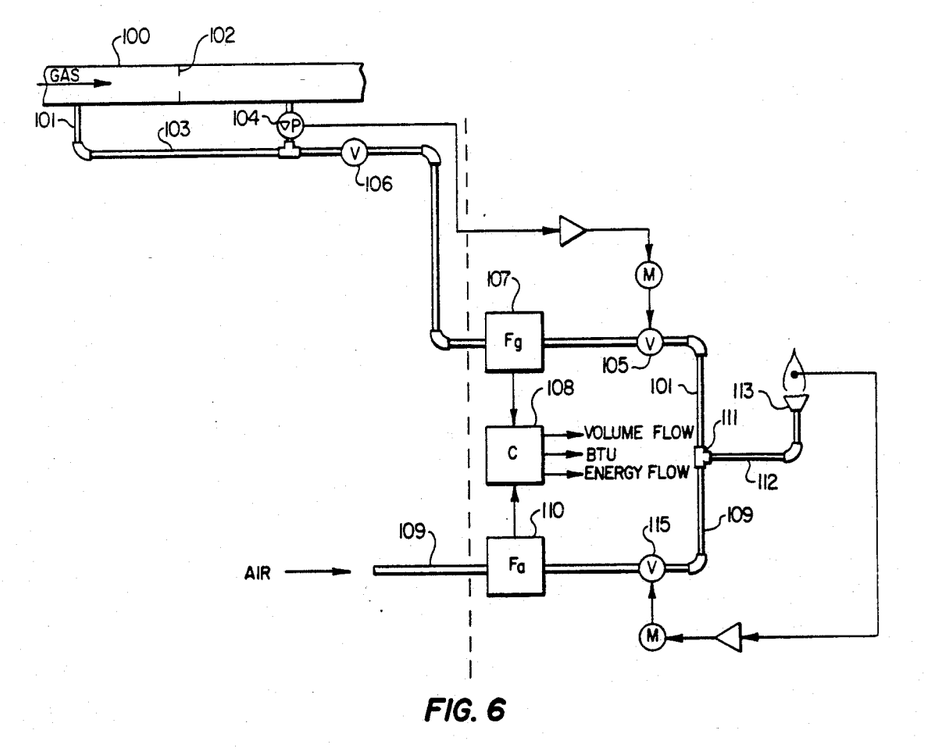
FIG. 6 is a diagrammatic elevational view of another embodiment of the invention.

Attention is now directed to FIG. 6 which illustrates another embodiment of the invention. In FIG. 6, a main pipeline is designated 100, while a branch or sample line is designated 101. An orifice plate 102 is mounted in the main line 100, and an orifice plate 103 in the sample line 101. The pressures downstream of orifice plates 102 and 103 are detected by a differential pressure sensor 104. The output signal from sensor 104 is amplified and employed to control a motorized valve 105 to adjust the gas flow to equalize the downstream main line and sample line pressures. Sample line 101 also contains a regulator valve 106 and a flowmeter 107 of suitable type, indicated diagrammatically as a box Fg. The output signals from the flowmeter 107 are delivered to a control computer 108, indicated diagrammatically as a box C.

An air line 109 is provided with a flowmeter 110, indicated diagrammatically as Box Fa, installed therein. Signals from the flowmeter 110 are delivered to the computer 108. The air line 109 and the sample line 101 joint at 111 to deliver a combustible mixture through a line 112 to a burner 113. A detector 114 is positioned in or adjacent the flame to detect maximum temperature (if a thermocouple) or stoichiometric point (if a zirconium dioxide detector). The signal from the detector 114 is amplified and employed to control a motorized valve 115 to adjust the air flow to the desired end point.

In operation, the gas flow rate reported by the flowmeter 107 (Fg) is proportional to volume flow in the pipeline 100; and the air flow rate reported by flowmeter 110 (Fa) is proportional to energy flow rate in the pipeline 100. The ratio of the air flow rate to the gas flow rate (Fa/Fg) is proportional to heat content per standard unit of volume. The computer 108 may be programmed to compute this ratio, as well as apply proportionality constants to place the data Fg, Fa, and Fa/Fg in the desired units.

In addition to providing a continuous measurement of energy flow in the pipeline, parts of the system can be used to measure volumetric flow in the pipeline. This can be done much more accurately with this invention than with state of the art methods. The output from conduit 14 (See FIG. 1) can be measured at ambient pressure with a volumetric displacement meter. With the correct proportionality constant this output can then give the integrated volume flow through the main pipeline 10 measured at standard conditions. A time derivative of this volume will give the flow rate. Such a determination of flow rate would be independent of gas properties and would require the measurement of only one parameter instead of several.

With special respect to the subject matter of this case as distinguished from its parents, there are a number of nonobvious design simplifications that may be effected in embodiments of the orifice flow splitter that in no way hinder its use in certain situations. For example, in embodiments of the orifice flow splitter the sample stream orifice can be set much smaller than all of the other diameters in the splitter. In fact, there could be constructed an entire family of designs where the main line flow is increased as the sample line orifice is reduced in diameter and where the flow through the sample line is the same for all of the splitter designs. In such a family, as the sample line orifice diameter becomes small and the main line flow becomes large, the sample line diameter becomes less and less critical in the design.

As the sample line orifice diameter becomes small and the sample flow remains the same, the pressure differential, [delta] P, across the orifice must increase. In the flow splitter designs described herein, the same pressure differential occurs across the main line orifice; thus, the main line flow must increase. Denoting sample line flow by $F_s$, main line diameter by $D_m$, and main line orifice diameter by $d_n$; $F_s$, $D_m$, and $d_n$ are fixed in the family of designs described herein. Using $D_s$ and $d_s$ to denote sample line diameter, and sample line orifice diameter respectively, as $d_s$ is decreased a certain value, $d_s°$, will be reached where the performance of the splitter is essentially independent of $D_s$ as long as $d_s \leq d_s°$ and $D_s \geq 10 d_s$. The value of $d_s°$ depends upon the values of $F_s$, $d_m$, and $D_m$.

The design regime of the present invention is useful for situations in which the ratio of main line flow to sample line flow is high, e.g., on the order of 100,000:1 or higher. For useful application of a splitter acording to the teachings of the present invention, the main line flow should have a Reynolds number that exceeds 100,000. This is true of most transmission pipelines but is generally not true in distribution systems. Thus, the present invention is a good candidate for incorporation into transmission lines where a high ratio of main line flow to sample line flow is required.

As is well known to those skilled in the art, if the main line flow Reynolds number exceeds 100,000 then to a first approximation:

$$F_m = (\pi/4) d_m^2 (0.61)(2 g_c \Delta P/\rho)^{\frac{1}{2}} / [1 - (d_m/D_m)^2]^{\frac{1}{2}} \quad \text{(Equation No. 54)}$$

where $g_c$ is the acceleration due to gravity and $\rho$ equals the gas density in the pipeline.

When the sample line orifice is small then the main frictional effects are the contraction of the gas to pass through the orifice and sudden enlargement of the diameter downstream of the orifice. In such a case the equation set forth in the immediately preceding paragraph is no longer the appropriate equation because of the very low ratio of orifice to pipe diameters. The inventors of the present invention hereby teach using equations which involve a sudden enlargement and a sudden contraction of flow due to a diameter change. Using such equations, one has for the isothermal flow of an ideal gas:

$$F_s = (\pi/4) d_s^2 [(4/3) g_c \Delta P/\rho]^{\frac{1}{2}} \quad \text{(Equation No. 55)}$$

The equation immediately above assumes that $d_s/D_s < 0.1$ and that the orifice has negligible length. If the orifice does have length of several diameters then the equation above should be modified by a multiplicative constant.

Dividing equation No. 54 by equation No. 55 gives:

$$F_m/F_s = (0.747)(d_m/d_s)^2 / [1 - (d_m/D_m)^2]^{\frac{1}{2}} \quad \text{(Equation No. 56)}$$

Thus, the split, $F_m/F_s$, for the special design described hereinabove is independent of the main line flow or gas composition.

As those skilled in the art should now fully appreciate, the present invention describes a flow splitter in which sample in orifice diameter is set much smaller than main line, sample line, and main line orifice diameters. Such an interrelationship of diameters causes the sample line diameter to become less and less critical as main line flow increases, renders the split ($F_m/F_s$) independent of the main line flow and gas composition, and generally provides an improved method and apparatus for taking proportional samples of flowing gas in main lines having Reynolds numbers that exceed 100,000.

Obviously, numerous modifications and variations are possible in view of the above teachings. Accordingly, within the scope of the appended claims, the present invention may be practiced otherwise than as specifically described herein.

What is claimed is:

1. A method of taking a flowing sample of an at least substantially ideal gas at least substantially isothermally flowing through a line, which flowing sample is constantly proportionate to the flow rate of said flowing gas, said method comprising:
    a) passing said gas flowing through said line through a first flow restriction in said line;
    b) drawing a flowing sample of said gas from said line at a point upstream of said first flow restriction into a sample line;
    c) passing said flowing sample of said gas in said sample line through a second flow restriction in said sample line, the interior of said line, said first flow restriction, said sample line, and said second flow restriction each being substantially cylindrical, the interior diameter of each of the four elements above being sequentially identified by the following symbols: $D_{15}$, $d_{15}$, $D_{12}$, and $d_{12}$;
    d) equalizing the pressures downstream of said first and second restrictions; and
    e) $d_{12}$ being much less than $D_{15}$, $d_{15}$ and $D_{12}$ so that the flow through said line divided by the flow through said sample line is about $(0.747)(d_{15}/d_{12})^2 / [1 - (d_{15}/D_{15})^2]^{\frac{1}{2}}$.

2. A method as recited in claim 1, wherein said equalizing of downstream pressures is achieved by detecting the difference between said pressures and operating a valve in said sample line in a direction to eliminate said difference.

3. An apparatus for taking a constantly proportional flowing sample of an at least substantially ideal gas at least substantially isothermally flowing through a line having a first flow restriction therein, said apparatus comprising:
    means for drawing a flowing sample of gas from said line at a point upstream of said first flow restriction into a sample line;
    a second flow restriction within said sample line, said second flow restriction being much smaller than said first flow restriction so that the flow through said line divided by the flow through said sample line is about $$(0.747)(d_{15}/d_{12})^2/[1-(d_{15}/D_{15})^2]^{\frac{1}{2}}$$

wherein said lines and restrictions are all substantially cylindrical and where $d_{15}$ is the interior diameter of said first flow restriction, $d_{12}$ is the interior diameter of said second flow restriction, and $D_{15}$ is the interior diameter of said line; and means for equalizing the pressures downstream of said first and second restrictions.

4. An apparatus as recited in claim 3, wherein said line flow has a Reynolds number that exceeds 100,000.

5. An apparatus as recited in claim 3 wherein said means for equalizing the pressures downstream of said first and second restrictions comprises a valve in said sample line.

6. An apparatus as recited in claim 5, wherein said equalizing of downstream pressures is achieved by detecting the difference between said pressures and operating said valve in a direction to eliminate said difference.

* * * * *